(12) United States Patent
Abunassar

(10) Patent No.: US 10,675,439 B2
(45) Date of Patent: Jun. 9, 2020

(54) HIGH TORSION DELIVERY CATHETER ELEMENT

(71) Applicant: Abbott Cardiovascular Systems Inc., Santa Clara, CA (US)

(72) Inventor: Chad Abunassar, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 157 days.

(21) Appl. No.: 15/438,555

(22) Filed: Feb. 21, 2017

(65) Prior Publication Data
US 2018/0235657 A1  Aug. 23, 2018

(51) Int. Cl.
| | | |
|---|---|---|
| *A61M 25/00* | (2006.01) | |
| *A61F 2/24* | (2006.01) | |
| *A61M 25/01* | (2006.01) | |
| *A61B 17/00* | (2006.01) | |
| *A61B 1/008* | (2006.01) | |

(52) U.S. Cl.
CPC ....... *A61M 25/0054* (2013.01); *A61F 2/2466* (2013.01); *A61B 1/008* (2013.01); *A61B 2017/00314* (2013.01); *A61M 25/0138* (2013.01)

(58) Field of Classification Search
CPC ............. A61F 2/2466; A61M 25/0054; A61M 25/0138; A61B 17/3468; A61B 2017/00314; A61B 1/008
See application file for complete search history.

(56) References Cited

U.S. PATENT DOCUMENTS

| | | | |
|---|---|---|---|
| 5,042,707 | A | 8/1991 | Taheri et al. |
| 5,386,741 | A | 2/1995 | Rennex |
| 7,338,505 | B2 | 3/2008 | Belson |
| 7,553,275 | B2 | 6/2009 | Padget et al. |
| 7,637,903 | B2 | 12/2009 | Lentz et al. |

(Continued)

FOREIGN PATENT DOCUMENTS

| | | |
|---|---|---|
| WO | 2010149969 A1 | 12/2010 |
| WO | WO 2016/176610 A1 | 11/2016 |

OTHER PUBLICATIONS

European Patent Office, International Search Report, dated May 7, 2018, pp. 1-5.

(Continued)

*Primary Examiner* — Amber R Stiles
(74) *Attorney, Agent, or Firm* — Baker Botts L.L.P.

(57) ABSTRACT

A jointed system for delivering a medical device to a target location within a human anatomy, comprising: a first segment that is a hollow cylinder, wherein a first flange and a second flange are attached to the distal end and extend distally away from the first segment; a second segment that is a hollow cylinder and has a proximal end and a distal end, wherein a third flange and a fourth flange are attached to the proximal end and extend proximally away from the second segment; a connector element having four cylindrical lugs extending radially away from a central point, wherein each lug passes, respectively, through a circular hole, and further wherein the connector element defines at least two separate openings extending in a direction from the distal end of the first segment to the proximal end of the second segment.

17 Claims, 8 Drawing Sheets

(56) References Cited

U.S. PATENT DOCUMENTS

| | | |
|---|---|---|
| 7,708,102 B2 | 5/2010 | Takehara et al. |
| 8,052,607 B2 | 11/2011 | Byrd |
| 8,096,457 B1 | 1/2012 | Manoux et al. |
| 8,721,591 B2 | 5/2014 | Chang et al. |
| 8,852,112 B2 | 10/2014 | Bielewicz et al. |
| 2002/0062062 A1 | 5/2002 | Belson et al. |
| 2002/0082585 A1 | 6/2002 | Carroll |
| 2003/0036748 A1* | 2/2003 | Cooper ............ A61B 17/00234 606/1 |
| 2003/0083550 A1 | 5/2003 | Miyagi |
| 2005/0107667 A1 | 5/2005 | Danitz et al. |
| 2006/0111616 A1 | 5/2006 | Danitz |
| 2006/0199999 A1* | 9/2006 | Ikeda ................ A61B 1/00149 600/141 |
| 2008/0051703 A1 | 2/2008 | Thornton et al. |
| 2008/0287741 A1 | 11/2008 | Ostrovsky |
| 2009/0099554 A1 | 4/2009 | Forster |
| 2009/0171151 A1 | 7/2009 | Choset et al. |
| 2011/0022078 A1 | 1/2011 | Hinman |
| 2011/0319898 A1* | 12/2011 | O'Neil ............... A61B 17/1671 606/84 |
| 2012/0136350 A1 | 5/2012 | Goshgarian et al. |
| 2012/0190924 A1 | 7/2012 | Tseng |
| 2014/0135685 A1 | 5/2014 | Kabe et al. |
| 2015/0226269 A1* | 8/2015 | Katsuragi ............... F16D 1/068 464/106 |
| 2017/0095922 A1* | 4/2017 | Licht ....................... B25J 9/065 |

OTHER PUBLICATIONS

International Search Report and Written Opinion dated Apr. 10, 2017 in International Application No. PCT/US2017/016781 ISA, PCT Search Report, p. 1-7.

International Search Report dated Jul. 18, 2013 in International Application No. PCT/US2013/038073.

* cited by examiner

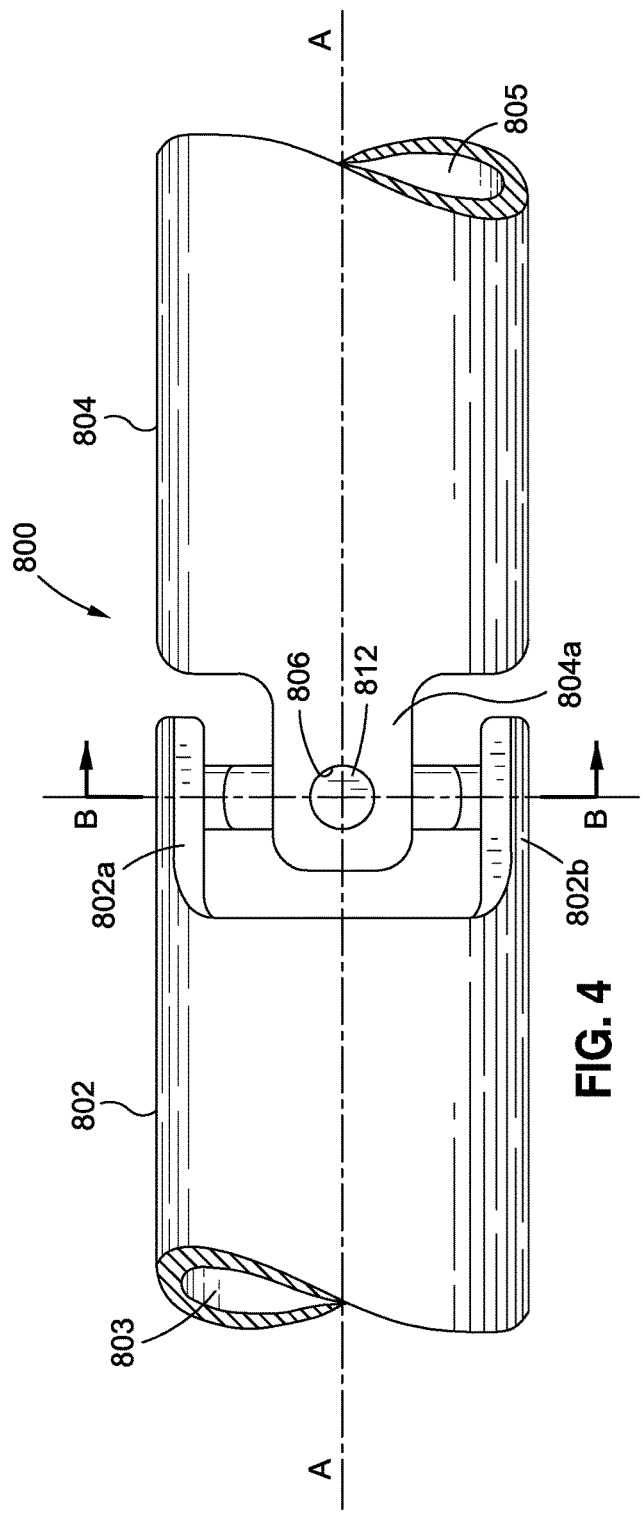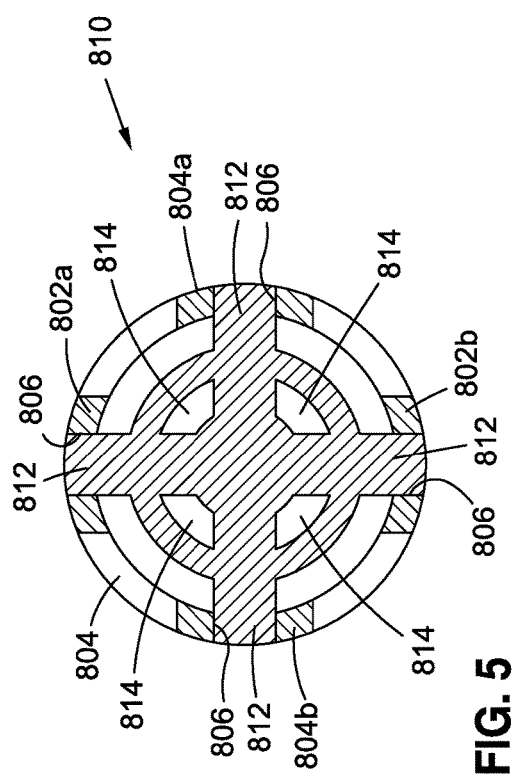

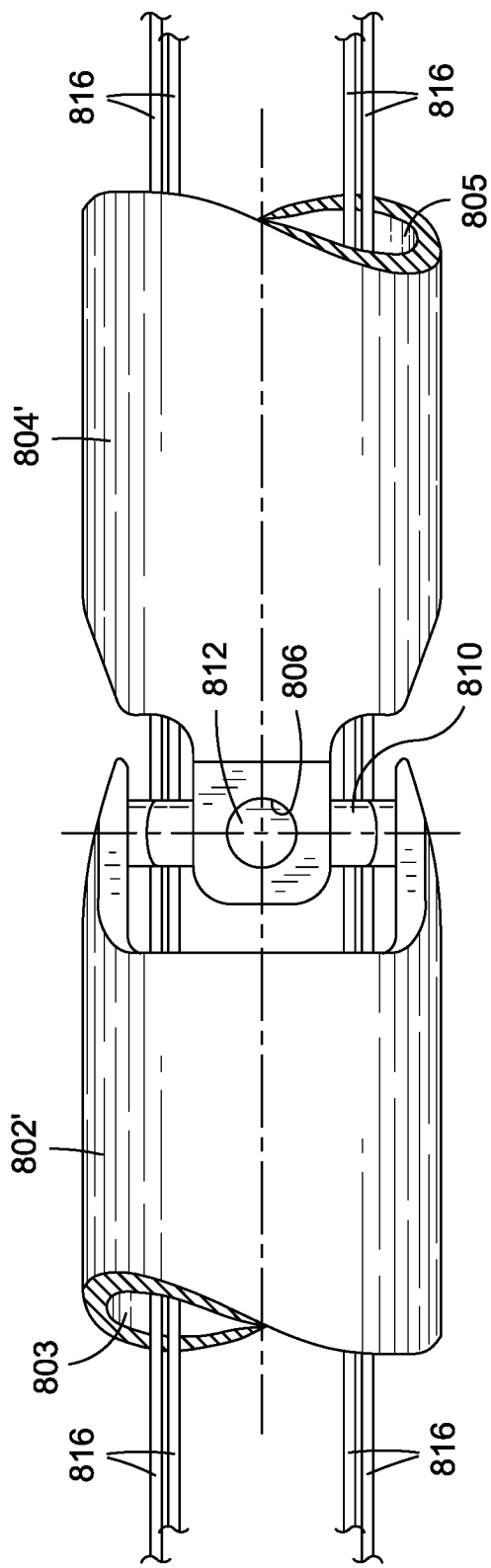
FIG. 6
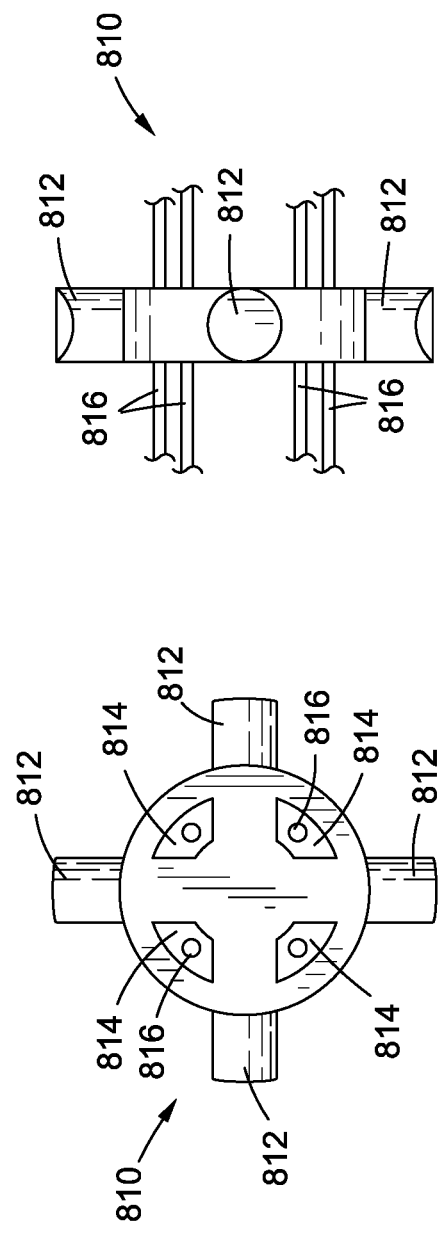
FIG. 7
FIG. 8

HIGH TORSION DELIVERY CATHETER ELEMENT

BACKGROUND

This application relates to systems and methods for implanting devices such as replacement heart valves, valve repair devices such as clips, stents, and similar therapeutic devices within the anatomy of a patient.

It is well known in the art to implant devices such as replacement heart valves, valve repairing clips, stents, reinforcement rings, and the like into the human heart to restore its function. Similar devices are also introduced into other parts of the human anatomy where mechanical repair is needed. Many such repair operations are carried out by first inserting a steerable delivery catheter by minimally invasive means into a desired organ of the human anatomy. Thereafter, a repair device positioned on the distal tip of a delivery element is passed through an internal lumen along the entire length of the delivery catheter until the repair device reaches the target organ, and the device is pushed out of the distal end of the catheter for implantation. Such repair devices may expand to assume a new shape once they are pushed out of the delivery catheter, some by means of self-expansion, others by means of mechanical expansion via balloons, expanders, actuators, and the like.

One of the problems confronted by such systems known in the art is that the steerable delivery catheter (also referred to as a steerable sleeve, or steerable guide catheter) may require to be threaded through a tortuous series of twists and turns through one or more lumens in the patient's anatomy. Once the delivery catheter is in position, the repair device at the tip of a delivery element must be pushed up, in a manner controlled from outside the patient, through a lumen of this tortuously twisted delivery catheter. When a normally straight delivery element is advanced through this curved sleeve with an implant at its distal tip, substantial bending forces develop between the sleeve and the delivery element, which results in substantial rubbing and friction between the delivery element and the curved steerable sleeve. This buildup of friction is problematic and, when twisting the proximal handle, only a portion of torque is likely to transmit to the distal end of the delivery element. Further, the transfer of this torque is irregular and requires "Dottering" (named after pioneer interventionalist Dr. Charles Dotter) to release stored torque as the system sticks and slips. As a result of this cumbersome transfer of torque through the system, an operator has a difficult time rotating the medical implant device at the tip of the delivery system with the degree of accuracy needed to efficiently position the repair device without overshooting. In terms of design, the delivery element must be stiff enough to transmit torque; however, it must also be flexible to avoid accumulating bending forces that result in friction loss.

By way of more detailed description, and referring to FIG. 1, there is shown a schematic frontal illustration, looking posteriorly from the anterior side of a patient 100. The heart 102 is a pump, the outlet of which is the aorta, including the descending aorta 104, which is a primary artery in the systemic circulation. The circulatory system, which is connected to the heart 102 further comprises the return, or venous, circulation. The venous circulation comprises the superior vena cava 108 and the inferior vena cava 106. The right and left jugular veins, 110 and 112, respectively, and the subclavian vein 114 are smaller venous vessels with venous blood returning to the superior vena cava 108. The right and left femoral veins, 116 and 118 respectively, return blood from the legs to the inferior vena cava 106. The veins carry blood from the tissues of the body back to the right heart, which then pumps the blood through the lungs and back into the left heart. The arteries of the circulatory system carry oxygenated blood (not shown) from left ventricle of the heart 102 to the tissues of the body.

FIG. 2 (prior art) shows that a vascular introduction sheath 204 has been inserted into the right femoral vein 116 via a percutaneous puncture or incision. A guidewire 200 has been inserted through the introduction sheath 204 and routed up the inferior vena cava 106 to the right atrium 202, one of the chambers of the heart 102. In this illustration, the left anatomical side of the patient 100 is toward the right. The guidewire 200 has been placed so that it can be used to track a delivery catheter into a region of the heart 102.

FIG. 3 (prior art) shows how, after the placement of a guidewire 200 into the left atrium of the patient's heart by known means, a delivery catheter 700, or sleeve, having an open central bore 704 may be advanced over the guidewire until a distal tip of the guide catheter is positioned in the left atrium. The purpose of the delivery catheter 700 shown in FIG. 3 is to permit a delivery element to advance and introduce a tool such as a clip, stent, valve, or the like, via a central bore of the guide catheter, into the left atrium for eventual placement in the heart via a puncture in the septum 504, for example, into the mitral valve 510. Tools such as these are typically introduced at the distal end of an delivery element. FIG. 3 shows the extremely tortuous radius of a guide catheter, through which a delivery element must be forced axially, and made to rotate while being forced axially.

For the most tools, accurate translational and rotational positioning and control are vital to procedural success, so attempts have been made to torsionally stiffen the delivery catheter to more reliably transmit torque from the proximal handle to the distal tip of the catheter. Unfortunately, conventional designs that aim to torsionally stiffen the delivery element naturally also increase the bending stiffness and thus increase friction interactions between the delivery catheter and sleeve. This potentially worsens the problems associated with friction buildup, such as stored torque, and poor transfer of torque. If a device is interacting with delicate anatomic structures, such as valve leaflets, friction-induced motion instabilities may lead to unintended injury or sub-optimal device placement.

Therefore, due to the problems described above, it is desired to have a delivery element that is reasonably easy to construct and that can transfer maximum torque, while also having minimum bending stiffness. The present invention addresses these and other needs.

SUMMARY OF THE INVENTION

In one embodiment, the invention is a jointed system for delivering a medical device to a target location within a human anatomy. The jointed system comprises a first segment that is a hollow cylinder and has a proximal end and a distal end, wherein a first flange and a second flange are attached to the distal end and extend distally away from the first segment, further wherein the first flange is positioned diametrically across the first segment opposite the second flange. A second segment is provided, which is a hollow cylinder and has a proximal end and a distal end, wherein a third flange and a fourth flange are attached to the proximal end and extend proximally away from the second segment. Additionally, the third flange is positioned diametrically across the second segment opposite the fourth flange. Under this configuration, the distal end of the first segment is positioned adjacent the proximal end of the second segment such that each of the first flange and the second flange are positioned between the third flange and the fourth flange. Furthermore, each of the first flange, the second flange, the third flange, and the fourth flange, defines a circular hole. A connector element is provided, which has four cylindrical lugs extending radially away from a central point, wherein each lug passes, respectively, through each circular hole, and further wherein the connector element defines at least two separate openings extending in a direction from the distal end of the first segment to the proximal end of the second segment.

In some embodiments, the jointed system further includes at least two wires for controlling a medical device, each wire extending respectively through each separate opening. In some embodiments, the at least two separate openings are four openings in number. In yet further embodiments, the jointed system further includes a guiding catheter having a central bore, wherein the first segment, and the second segment are positioned within the central bore. In alternative embodiments, the first segment includes a cylindrical portion and an external surface which departs from a cylindrical form at a terminal end, wherein an outside surface the first segment slopes towards a central axis of the first segment by a distance D5 towards the axis over a distance D6 along the axis, wherein the ratio of D5:D6 is between ⅕ and ¼. The jointed system of claim 1, wherein the first segment has a length of D1 and a diameter of D2, wherein the ratio of D1:D2 is between 1.8 and 2.2. In yet further alternative embodiments, the first segment and the second segment are formed from a polymer, and alternatively, of a metal which is preferably stainless steel, elgiloy, or nitinol.

In another embodiment, the invention is a jointed system for delivering a medical device to a target location within a human anatomy. The invention comprises a first segment that is a hollow cylinder having a proximal end and a distal end, and a second segment that is a hollow cylinder having a proximal end and a distal end. Under this configuration, the distal end of the first segment is positioned adjacent the proximal end of the second segment, and further wherein the first segment is connected to the second segment by a connector element that has four lugs positioned in a single plane, and a first set of two lugs are inserted into holes defined by the first segment and a second set of two lugs are inserted into holes defined by the second segment. A sheath is provided which surrounds, and in sliding contact with, the first segment and the second segment.

In some embodiments, the connector element defines at least two separate openings extending in a direction from the distal end of the first segment to the proximal end of the second segment. In yet further embodiments, the four lugs are positioned at ninety degree intervals around a circumference of the connector element. In even further embodiments, the first segment includes a cylindrical portion, and an external surface which departs from a cylindrical form at its proximal end, wherein an outside surface the first segment slopes towards a central axis of the first segment by a distance D5 towards the axis over a distance D6 along the axis, wherein the ratio of D5:D6 is between ⅕ and ¼. In other embodiments again, the first segment has a length of D1 and a diameter of D2, wherein the ratio of D1:D2 is between 1.8 and 2.2.

These and other advantages will become apparent when read in conjunction with the drawings and the detailed description of embodiments.

BRIEF DESCRIPTION OF THE DRAWINGS

FIG. 4 is a perspective view, in partial cutaway, of aspects of a delivery element having features of the invention.

FIG. 5 is a sectional view taken substantially along the line B-B in FIG. 4.

FIG. 6 is a perspective view, in partial cutaway, of another embodiment of the delivery element shown in FIG. 4.

FIG. 7 is a vertical front view of an element of the invention.

FIG. 8 is a vertical side view of the element in FIG. 7.

DETAILED DESCRIPTION OF THE EMBODIMENTS

Figure 1:
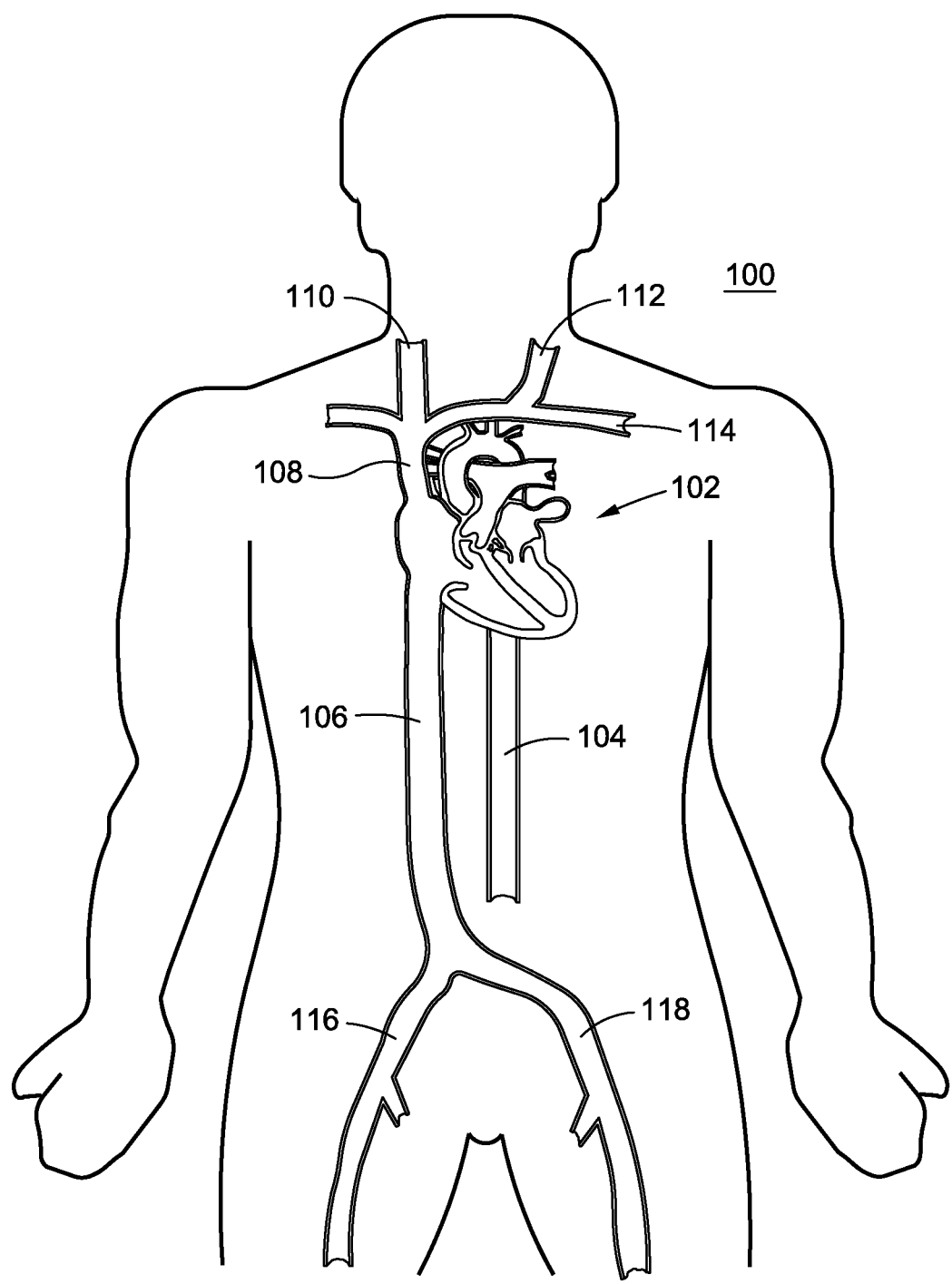
FIG. 1 is a front view schematic representation of the human venous circulatory system including the heart and the great veins.
Figure 2:
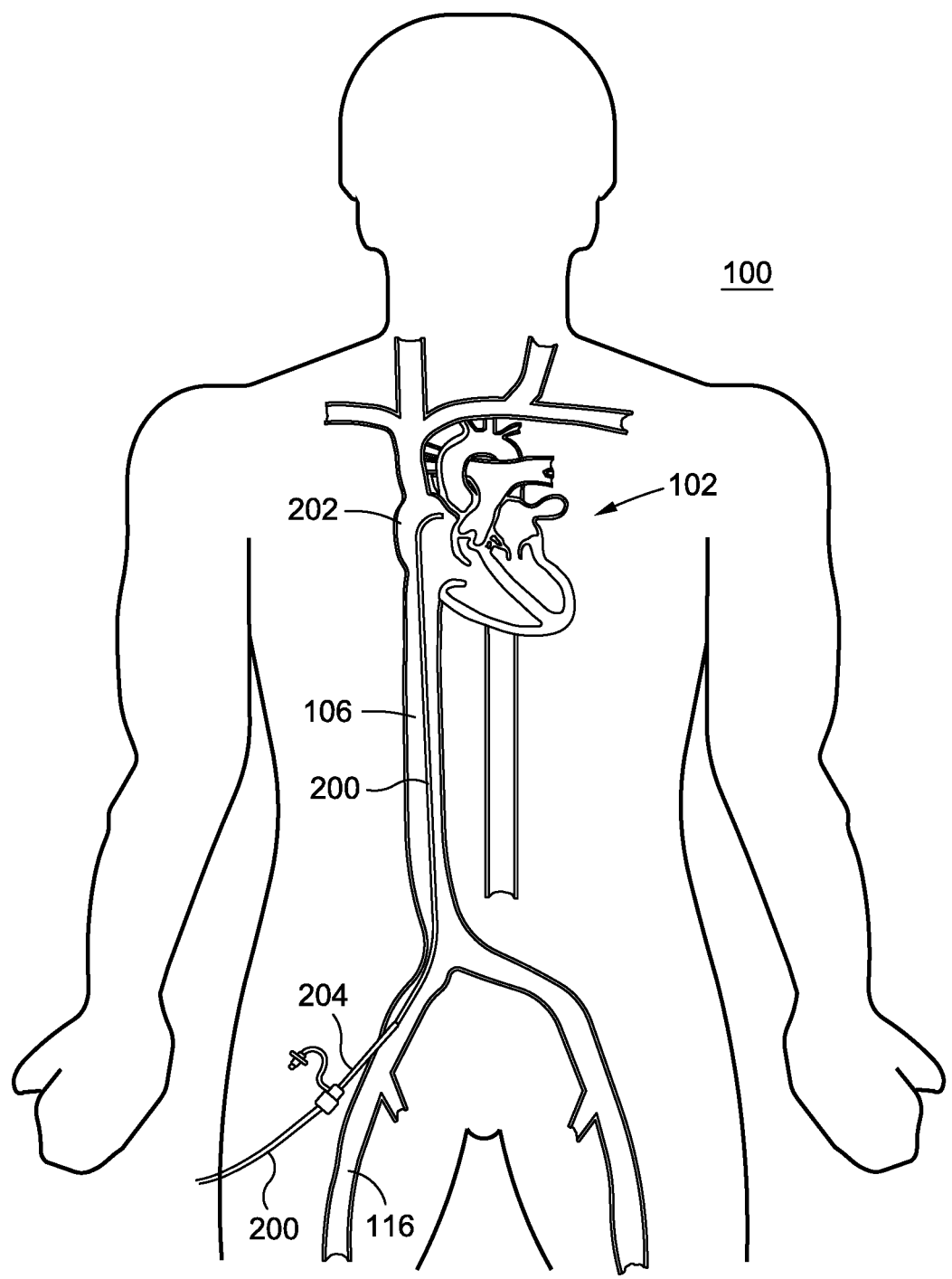
FIG. 2 is a front view schematic representation of the human venous circulatory system with a known guidewire routed from the femoral vein into the right atrium.
Figure 3:
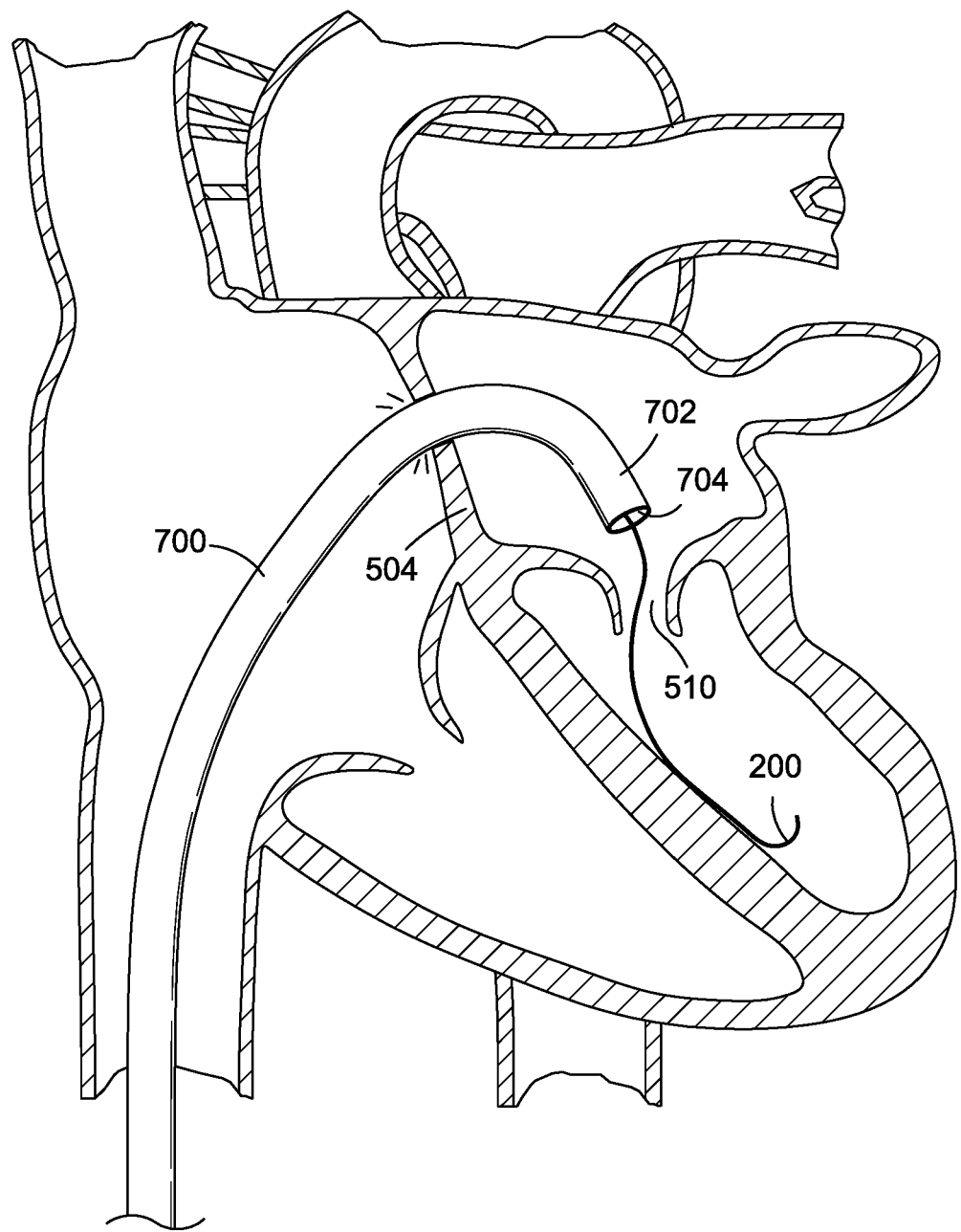
FIG. 3 is a front view schematic representation of the human venous circulatory system with a guide catheter advanced into the left atrium of a patient's heart, via a septal puncture.

As may be understood from this detailed description, as read in conjunction with the figures, a delivery system for transcatheter delivery, having features of the invention, is described. The context of the invention is explained above with initial reference to FIGS. 1-3.

With reference now to FIGS. 4-11, in some embodiments the invention includes a jointed system 800 for a delivery element suitable for use in delivering medical repair devices. In a preferred embodiment, the invention includes a first cylindrical segment 802 which is hollow, having a central bore 803 and a second cylindrical segment 804 which is hollow, having a central bore 805. Each of these cylindrical segments may be made from a metal or from a polymer, and may be cut from a parent cylinder using known micro-cutting means such as laser energy and micro-drilling. In other cases cylindrical segments may be constructed of braided or composite shafts or polymer extrusions with any number of internal lumens.

As may be seen in FIG. 4, the first cylindrical segment 802 is positioned adjacent to, and coaxially aligned with, the second cylindrical segment 804. Each one of the adjacent ends of each segment is shaped to have a set of two flanges that extend away from each respective segment in a direction parallel with the elongate axis A-A that is shared by the two segments. As seen in FIG. 4, first segment 802 has a set of two flanges 802a, 802b, and second segment 804 has a set of two flanges 804a, 804b. Each of the two flanges in a set are located on opposite sides (that is, 180 degrees apart) of the associated cylindrical segment. When the jointed system 800 is assembled, the first segment 802 is rotated 90 degrees around the shared axis A-A in relation to the second segment 804, so that the two sets of flanges fit adjacent one another in a circumferential direction, as seen in FIG. 4.

However, before the jointed system is assembled, the two segments 802, 804 are further processed. A circular hole 806 is drilled into each of the four flanges 802a, 802b, 804a,

804b. Each hole is drilled into each flange in a radial direction with respect to the respective segment, and is aligned with the hole on the opposing flange. Known systems for micro-drilling may be used, because the diameter of the hole 806 may be 0.4 to 1.0 mm, and it should be drilled circular with a constant radius to within a high degree of tolerance, as will become apparent hereafter.

As may be better understood with reference to FIGS. 5, 7 and 8, once the two cylindrical segments have been provided as described above, and before they are joined together, a third element is prepared. A connector element 810 is provided and introduced between the first segment 802 and the second segment 804 for facilitating their being connected together.

With reference to FIG. 5, FIG. 7, and FIG. 8, the connector element 810 is, from one view, a planar element (FIG. 8) and has four lugs 812 or pins that extend radially outwardly to an equal radial length away from a common center point. Thus, from an orthogonal view, the connector element 810 has a cruciform shape as seen in FIG. 7. The lugs 812 are prepared by known micro-milling technique to produce a cylindrical shape of the same radius in each lug. The radius of the lug is selected to be the same (within tolerance) as the radius of the hole 806 drilled into each flange. Further, in preferred embodiments, the cruciform element 810 defines a plurality of separate openings 814 (four, in the embodiment shown in FIG. 7) which will permit the passage of wires 816 (seen in FIGS. 6-9) for operating a medical device during implantation once the system has been assembled.

Once these elements are prepared, they are assembled as follows. The objective is to insert one of each of the four lugs 812 into one of each of the four holes 806—to cause the two cylindrical segments 802, 804 to be connected to each other. This action can be accomplished by squeezing the first cylindrical segment across a diameter, so that the two flanges on that segment move apart slightly. The connector element 810 is inserted between the flanges 802a, 802b and the lugs 812 are aligned with the holes 806, so that when the squeezing force is removed, the flanges return to the their normal separation, thereby inserting the lugs 812 into the holes 806. Next, the second cylindrical element 804 is squeezed across a diameter to open the space between the opposing flanges 804a, 804b. The remaining two lugs 812 are positioned adjacent and aligned with the remaining holes 806, whereupon the squeezing force is removed. This causes the segment to resume its normal cylindrical shape, and the lugs 812 to slide into the remaining holes 806. At this point, the four lugs of the connector element are snugly inserted into the four holes of the two segments 802, 804 and the assembly appears as in FIG. 4.

At this point, it will be appreciated that the two segments 802, 804 are joined together by a system that will provide a very high degree of torsional stiffness. This high degree of stiffness arises because the load bearing elements for carrying torsion from the first segment 802 to the second segment 804 comprise the respective lugs and holes. These lugs and holes are located at a very large radial distance away from the central axis A-A of the assembly. In fact, they are located at the outer perimeter of the assembly, and this provides a high degree of mechanical advantage in rotating the jointed system. Furthermore, the arrangement provides for a very high level of mobility in the jointed system that arises. If a little lubricant is applied at the holes, the frictional resistance at the joint is very low.

Therefore, it will be appreciated, if a series of segments are connected end to end using the foregoing jointing system, then the resulting structure presents a system that is highly flexible longitudinally, but torsionally very stiff. This is a highly advantageous structure for the purpose of catheter delivery via a guide catheter.

It will also be appreciated that the presence of the openings 814 in the connector element 810 for receiving control wires plays an advantageous role in confining any control wires that are selected to extend along the segment bores 803, 805. In the absence of such openings in the connector 810, the nature of the jointed system would present the two sets of flanges 802a, 802b and 804a, 804b which, when the two segments 802, 804 are rotated at an angle with respect to each other, would tend to come close to touching each other. In these circumstances, a control wire passing across the connector element 810 between the two segments may migrate radially outward to a location between two opposing flanges and become entrapped or damaged by the flanges. However, by provided dedicated openings 814 and by passing the wires through the openings which are closer to the center of the connector element 810, the wires are kept away from the perimeter of the joint, and are kept from becoming entrapped between the flanges.

Figure 9:
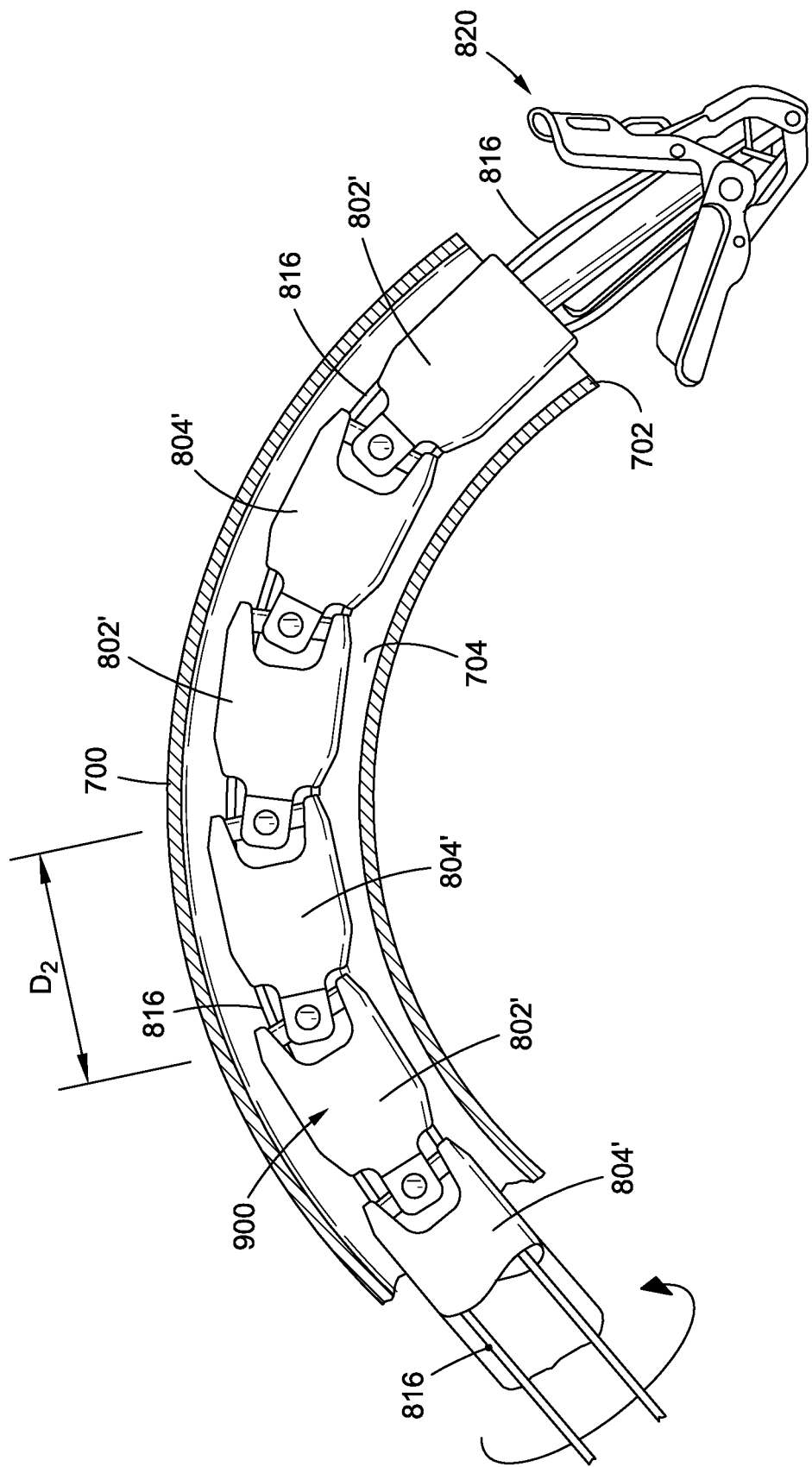
FIG. 9 is a schematic view in partial section of a delivery element having features of the invention.

Having described a jointed system 800 in FIGS. 4-5 and FIGS. 7-8, it will become apparent that a series of segments may be connected to each other, end to end, as seen in FIG. 9, to form a delivery element 900. Each connection includes a repeating arrangement where a connector element 810 joins one segment to the next. Through the openings 814 in each of the connector elements may run a series of separate wires 816 which are configured for operating a medical device 820 at the distal end of the series of segments. FIG. 9 shows how the connected segments form a delivery element 900 which may be inserted into a central bore 704 of a delivery catheter 700, and how it may be pushed distally until the medical device 820 emerges from the distal end 702 of the delivery catheter. It will be appreciated that the four lug connections each possess: (1) great torsional stiffness, so that there is a high degree of fidelity between rotational movement at the proximal end of the delivery element 900 and rotational movement by the medical device 820; (2) great axial stiffness, so that there is a high degree of fidelity between axial movement at the proximal end of the delivery element and axial movement by the medical device 820; and (3) great bending flexibility, so that the four lug connection permits near frictionless bending about two axes of rotation simultaneously.

A note that is applicable here is that the four lug connections should only be present within the length of the delivery catheter that remain positioned within the steerable guide catheter throughout the use of the catheter. As a device is advanced forward toward the valve plane or below, if a four lug connection becomes exposed distal to the guide, all control would be lost since there is no bending stiffness in the connection acting on its own. For this reason, an "extendable" dimension at the distal portion of the catheter (just proximal to the device being delivered) should remain rigid without joints so that the exit trajectory of the device is trustworthy during device advancement.

An important dimension in the overall behavior of the delivery element is the length of each of the segments. The shorter each segment, the tighter (i.e. smaller) the radius of curvature that the delivery element will be able to follow in going round the curved delivery catheter 700.

Figure 10:
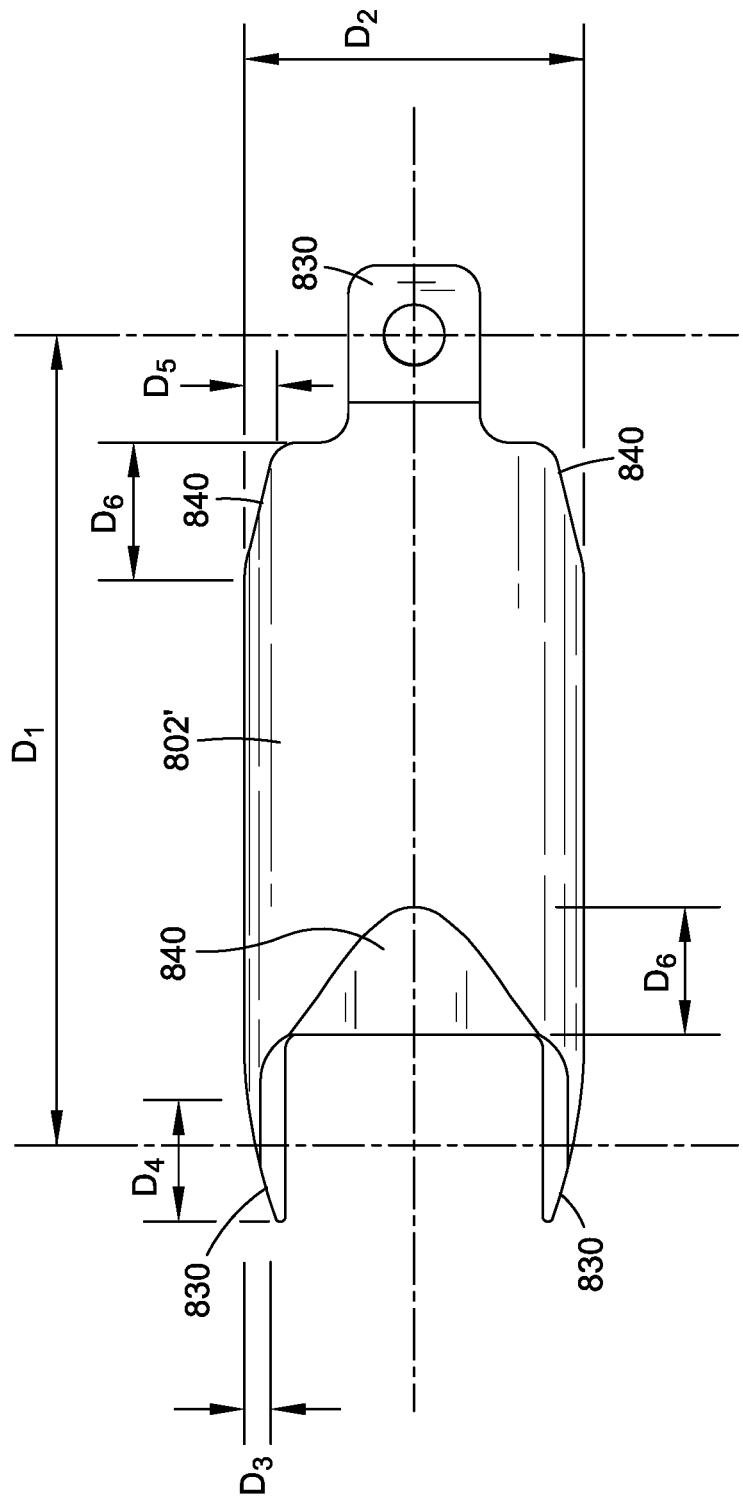
FIG. 10 is a perspective view of a component of a delivery element having features of the invention.

Another geometric property of the segments that affects the amount of frictional drag against both rotation and advancement of the delivery element through the delivery catheter is the shape of the outer surface of the segments. An improvement that may be imparted to each segment is to slope the ends of each segment towards the axial centerline of each segment, as seen in FIG. 6 and FIG. 10. In this embodiment, segments forming the jointed system are referred to as 802' and 804'. This has the advantage that, when the delivery element 900 is pushed around a corner of the delivery catheter and then advanced along the bore of the delivery catheter 700, the terminal ends of the segment do not snag into the inner surface of the delivery catheter. In a preferred embodiment, the shape of each segment may be described as follows: (1) The ends 830 of each flange slope towards the central axis of the segment at an angle having a slope given by the distance D3 divided by the distance D4, which is preferably between ⅕ and ¼. D3 is the distance (in a radial direction) by which the outside of the cylindrical form departs from the purely cylindrical, and D4 is the distance (in an axial direction) over which the departure takes place. (2) The outside of surface of each segment, located between the two flanges, also slopes towards the central axis of the segment at an angle having a slope given by the distance D5 divided by the distance D6, which is preferably between ⅕ and ¼. D5 is the distance (in a radial direction) by which the outside of the cylindrical form departs from the purely cylindrical, and D6 is the distance (in an axial direction) over which the departure takes place. It will be appreciated, with reference to FIG. 9 and FIG. 11, that by providing these tapered or sloping surfaces, the extremities of the segments 802, 804 will, when the segments are bent out of line with each other, be able to rotate more smoothly inside a delivery catheter 700 as the medical device 820 is being positioned in the patient's anatomy.

Figure 11:
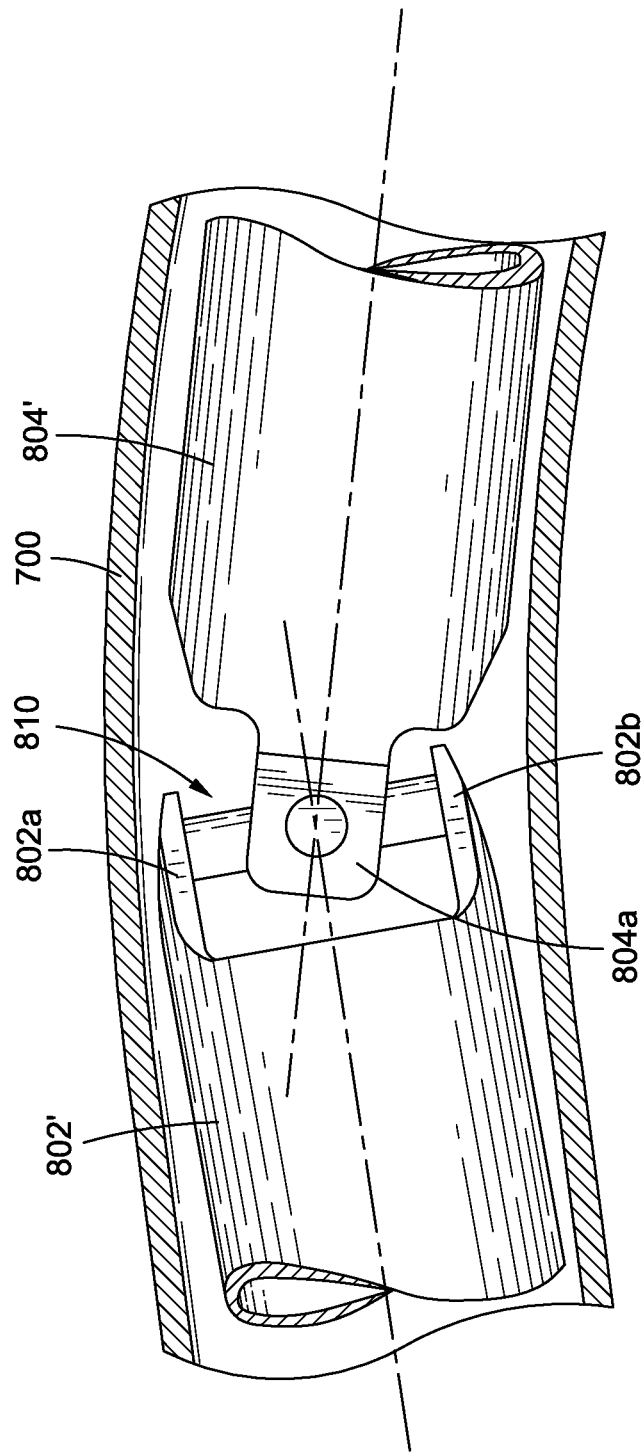
FIG. 11 is a perspective view, in partial cutaway, of the embodiment in FIG. 6, shown in a bent condition.

With reference to FIGS. 9-11, it will be appreciated that the length D1 of each segment in relation to its diameter D2 will play an important role in enabling a chain of connected segments to pass around a curved delivery catheter 700, and to be rotated at the same time. In a preferred embodiment, the aspect ratio (D1/D2) of each segment preferably is in the range of between 1.8 and 2.2.

Thus, a novel and advantageous system for delivering an implant through a tortuous guide catheter is described that addresses problems in the art. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

I claim:

1. A jointed system for delivering a medical device to a target location within a human anatomy, comprising:
    a first segment that includes a first hollow cylinder and has a proximal end and a distal end, wherein the distal end of the first hollow cylinder is shaped to define a first flange and a second flange, each extending distally away from the first segment, further wherein the first flange is positioned diametrically across the first segment opposite the second flange, and wherein the first hollow cylinder, first flange and second flange collectively define a cylindrical form;
    a second segment that includes a second hollow cylinder and has a proximal end and a distal end, wherein the proximal end of the second hollow cylinder is shaped to define a third flange and a fourth flange, each extending proximally away from the second segment, further wherein the third flange is positioned diametrically across the second segment opposite the fourth flange, and wherein the second hollow cylinder, third flange and fourth flange collectively define a cylindrical form;
    wherein the distal end of the first segment is positioned adjacent the proximal end of the second segment such that each of the first flange and the second flange are positioned between the third flange and the fourth flange, further wherein each of the first flange, the second flange, the third flange, and the fourth flange has a circular hole defined therein;
    a connector element having four cylindrical lugs extending radially away from a central point, wherein each lug passes, respectively, through the circular hole of a respective one of the first flange, second flange, third flange and fourth flange, and further wherein the connector element defines at least two separate openings extending in a direction from the distal end of the first segment to the proximal end of the second segment; and
    a guiding catheter having a central bore, wherein the first segment and the second segment are positioned within the central bore and moveable distally therethrough.

2. The jointed system of claim 1, further including at least two wires for controlling a medical device, each wire extending respectively through each separate opening.

3. The jointed system of claim 1, wherein the at least two separate openings are four openings in number.

4. The jointed system of claim 1, wherein the first segment includes a portion, of an external surface which departs from the cylindrical form at a terminal end, wherein an outside surface the first segment slopes towards a central axis of the first segment by a distance D5 towards the axis over a distance D6 along the axis, wherein the ratio of D5:D6 is between ⅕ and ¼.

5. The jointed system of claim 1, wherein the first segment has a length of D1 and a diameter of D2, wherein the ratio of D1:D2 is between 1.8 and 2.2.

6. The jointed system of claim 1, wherein the first segment and the second segment are formed from a polymer.

7. The jointed system of claim 1, wherein the connector element is formed from a metal.

8. The jointed system of claim 7, wherein the metal includes an alloy selected from one of stainless steel, elgiloy, and nitinol.

9. The jointed system of claim 1, wherein the proximal end of the first hollow cylinder is shaped to define a fifth flange and a sixth flange, each extending proximally away from the first segment, further wherein the fifth flange is positioned diametrically opposite the sixth flange, and wherein the fifth flange is offset from the first flange by 90 degrees about the cylindrical form.

10. The jointed system of claim 1, wherein the distal end of the second hollow cylinder is shaped to define a seventh flange and an eighth flange, each extending distally away from the second segment, further wherein the seventh flange is positioned diametrically opposite the eighth flange, and wherein the seventh flange is offset from the first flange by 90 degrees about the cylindrical form.

11. A jointed system for delivering a medical device to a target location within a human anatomy, comprising:
    a first segment that includes a first hollow cylinder having a proximal end and a distal end, wherein the distal end of the first hollow cylinder is shaped to define a first flange and a second flange, each extending distally away from the first segment, and wherein the first hollow cylinder, first flange and second flange collectively define a cylindrical form, a second segment that includes a second hollow cylinder having a proximal end and a distal end, wherein the proximal end of the second hollow cylinder is shaped to define a third flange and a fourth flange, each extending proximally away from the second segment, and wherein the second hollow cylinder, third flange and fourth flange collectively define a cylindrical form, wherein the distal end of the first segment is positioned adjacent the proximal end of the second segment, and further wherein the first segment is connected to the second segment by a connector element that has four lugs positioned in a single plane, and a first set of two of the four lugs are inserted into holes defined by the first segment and a second set of two of the four lugs are inserted into holes defined by the second segment; and a guiding catheter surrounding the first segment and the second segment, wherein the first and second segments are moveable distally therethrough.

12. The jointed system of claim 11, wherein the connector element defines at least two separate openings extending in a direction from the distal end of the first segment to the proximal end of the second segment.

13. The jointed system of claim 11 wherein the four lugs are positioned at ninety degree intervals around a circumference of the connector element.

14. The jointed system of claim 11, wherein the first segment includes a portion, of an external surface which departs from the cylindrical form at its proximal end, wherein an outside surface of the first segment slopes towards a central axis of the first segment by a distance D5 towards the axis over a distance D6 along the axis, wherein the ratio of D5:D6 is between $\frac{1}{5}$ and $\frac{1}{4}$.

15. The jointed system of claim 11 wherein the first segment has a length of D1 and a diameter of D2, wherein the ratio of D1:D2 is between 1.8 and 2.2.

16. The jointed system of claim 11, wherein the proximal end of the first hollow cylinder is shaped to define a fifth flange and a sixth flange, each extending proximally away from the first segment, further wherein the fifth flange is offset from the first flange by 90 degrees about the cylindrical form.

17. The jointed system of claim 11, wherein the distal end of the second hollow cylinder is shaped to define a seventh flange and an eighth flange, each extending distally away from the second segment, further wherein the seventh flange is offset from the first flange by 90 degrees about the cylindrical form.

* * * * *